United States Patent [19]

Shaw

[11] Patent Number: 4,904,584
[45] Date of Patent: Feb. 27, 1990

[54] SITE-SPECIFIC HOMOGENEOUS MODIFICATION OF POLYPEPTIDES

[75] Inventor: Gray Shaw, Bedford, Mass.

[73] Assignee: Genetics Institute, Inc., Cambridge, Mass.

[21] Appl. No.: 137,043

[22] Filed: Dec. 23, 1987

[51] Int. Cl.⁴ .............................................. C12D 21/00
[52] U.S. Cl. ................................. 435/69.4; 424/85.1;
       435/69.5; 514/8; 530/351; 530/397; 530/410
[58] Field of Search ........................................ 435/68

[56] References Cited

U.S. PATENT DOCUMENTS

| | | | |
|---|---|---|---|
| 4,738,844 | 4/1988 | Bell | 435/68 |
| 4,751,077 | 6/1988 | Bell | 435/68 |
| 4,753,795 | 6/1988 | Bell | 435/68 |
| 4,762,914 | 8/1988 | Auron | 435/68 |
| 4,769,233 | 9/1988 | Bell | 435/68 |

Primary Examiner—Peter D. Rosenberg
Attorney, Agent, or Firm—David L. Berstein; Bruce M. Eisen

[57] ABSTRACT

A homogeneously modified protein is provided having one or more selected naturally occurring lysine residues replaced by a suitable amino acid, or having one or more lysine residues substituted for other amino acids or inserted into a polypeptide sequence, leaving selected lysine residues having $\epsilon$-amino groups in the protein and coupling amine reactive compounds to selected lysine residues. Methods for producing the selected homogeneously modified proteins and pharmaceutical compositions containing such proteins are provided.

3 Claims, 7 Drawing Sheets

FIGURE 1

```
5'                            TCTCTTTAATCACTACTCACAGTAACCTCAACTCCTGCCACA
-20                                                  -10
Met Tyr Arg Met Gln Leu Leu Ser Cys Ile Ala Leu Ser Leu Ala Leu
ATG TAC AGG ATG CAA CTC CTG TCT TGC ATT GCA CTA AGT CTT GCA CTT
     50
                   1                                          10
Val Thr Asn Ser Ala Pro Thr Ser Ser Ser Thr Lys Lys Thr Gln Leu
GTC ACA AAC AGT GCA CCT ACT TCA AGT TCT ACA AAG AAA ACA CAG CTA
        100
                             20
Gln Leu Glu His Leu Leu Leu Asp Leu Gln Met Ile Ser Asn Gly Ile
CAA CTG GAG CAT TTA CTT CTG GAT TTA CAG ATG ATT TCG AAT GGA ATT
            150                                     40
     30
Asn Asn Tyr Lys Asn Pro Lys Leu Thr Arg Met Leu Thr Phe Lys Phe
AAT AAT TAC AAG AAT CCC AAA CTC ACC AGG ATG CTC ACA TTT AAG TTT
                200
                         50                                   60
Tyr Met Pro Lys Lys Ala Thr Glu Leu Lys His Leu Gln Cys Leu Glu
TAC ATG CCC AAC AAG GCC ACA GAA CTG AAA CAT CTT CAG TGT CTA GAA
                    250
                                         70
Glu Glu Leu Lys Pro Leu Glu Glu Val Leu Asn Leu Ala Gln Ser Lys
GAA GAA CTC AAA CCT CTG GAG GAA GTG CTA AAT TTA GCT CAA AGC AAA
                        350
     80                                                  90
Asn Phe His Leu Arg Pro Arg Asp Leu Ile Ser Asn Ile Asn Val Ile
AAC TTT CAC TTA AGA CCC AGG GAC TTA ATC AGC AAT ATC AAC GTA ATA
                            350
                                    100
Val Leu Glu Leu Lys Gly Ser Glu Thr Thr Phe Met Cys Glu Tyr Ala
GTT CTG GAA CTA AAG GGA TCT GAA ACA ACA TTC ATG TGT GAA TAT GCT
                             400
     110                                         120
Asp Glu Thr Ala Thr Ile Val Glu Phe Leu Asn Arg Trp Ile Thr Phe
GAT GAG ACA GCA ACC ATT GTA GAA TTT CTG AAC AGA TGG ATT ACC TTT
                                450
                           130          133
Cys Gln Ser Ile Ile Ser Thr Leu Thr
TGT CAA AGC ATC ATC TCA ACA CTG ACT TGA TAA TTAAGTGCTTCCCACTTAAAA
                                500

CATATCAGGCCTTCTATTTATTTAAATATTTAAATTTTATATTTATTGTTGAATGTATGGTTT

GCTACCTATTGTAACTATTATTCTTAATCTTAAAACTATAAATATGGATCTTTTATGATTCTT

TTTGTAAGCCCTAGGGGCTCTAAAATGGTTTCACTTATTTATCCCAAAATATTTATTATTATG

TTGAATGTTAAATATAGTATCTATGTAGATTGGTTAGTAAAACTATTTAATAAATTTGATAAA

TATAAAAA
```

FIGURE 2

```
         9                       24                        39                       54
GATCCAAAC ATG AGC CGC CTG CCC GTC CTG CTC CTG CTC CAA CTC CTG GTC CGC
          MET Ser Arg Leu Pro Val Leu Leu Leu Leu Gln Leu Leu Val Arg (1)
           69                        84   [C]             99
CCC GGA CTC CAA GCT CCC ATG ACC CAG ACA ACG TCC TTG AAG ACA AGC TGG GTT
Pro Gly Leu Gln Ala Pro MET Thr Gln Thr Thr Ser Leu Lys Thr Ser Trp Val 114                      129                      144                      159
AAC TGC TCT AAC ATG ATC GAT GAA ATT ATA ACA CAC TTA AAG CAG CCA CCT TTG
Asn Cys Ser Asn MET Ile Asp Glu Ile Ile Thr His Leu Lys Gln Pro Pro Leu
                                                                                 50
              174                      189                      204
CCT TTG CTG GAC TTC AAC AAC CTC AAT GGG GAA GAC CAA GAC ATT CTG ATG GAA
Pro Leu Leu Asp Phe Asn Asn Leu Asn Gly Glu Asp Gln Asp Ile Leu MET Glu 219                      234                      249                      264
AAT AAC CTT CGA AGG CCA AAC CTG GAG GCA TTC AAC AGG GCT GTC AAG AGT TTA
Asn Asn Leu Arg Arg Pro Asn Leu Glu Ala Phe Asn Arg Ala Val Lys Ser Leu 279                      294                      309                      324
CAG AAC GCA TCA GCA ATT GAG AGC ATT CTT AAA AAT CTC CTG CCA TGT CTG CCC
Gln Asn Ala Ser Ala Ile Glu Ser Ile Leu Lys Asn Leu Leu Pro Cys Leu Pro
                                                                 100
              339                      354                      369
CTG GCC ACG GCC GCA CCC ACG CGA CAT CCA ATC CAT ATC AAG GAC GGT GAC TGG
Leu Ala Thr Ala Ala Pro Thr Arg His Pro Ile His Ile Lys Asp Gly Asp Trp
MET
         384                      399                      414                      429
AAT GAA TTC CGG AGG AAA CTG ACG TTC TAT CTG AAA ACC CTT GAG AAT GCG CAG
Asn Glu Phe Arg Arg Lys Leu Thr Phe Tyr Leu Lys Thr Leu Glu Asn Ala Gln
                                    130
              444                      459                    475        485         495
GCT CAA CAG ACG ACT TTG AGC CTC GCG ATC TTT T-AGTCCAACG TCCAGCTGT TCTCTGGGCC
Ala Gln Gln Thr Thr Leu Ser Leu Ala Ile Phe
                                    147

505         515         525         535         545         555         565
TTCTCACCAC AGCGCCTCGG GACATCAAAA ACAGCAGAAC TTCTGAAACC TCTGGGTCAT CTCTCACACA 575         585         595         605         615         625         635
TTCCAGGACC AGAAGCATTT CACCTTTTCC TGCGGCATCA GATGAATTGT TAATTATCTA ATTTCTGAAA 645         655         665
TGTGCAGCTC CCATTTGGCC TTGTGCGGTT GTGTTCTCA
```

FIGURE 3

```
       10         20         30         40         50
GAATTCCGGG AACGAAAGAG AAGCTCTATC TCCCCTCCAG GAGCCCAGCT ATG AAC TCC TTC
                                                      MET Asn Ser Phe 65                  80                  95                 110
TCC ACA AGC GCC TTC GGT CCA GTT GCC TTC TCC CTG GGG CTG CTC CTG GTG TTG
Ser Thr Ser Ala Phe Gly Pro Val Ala Phe Ser Leu Gly Leu Leu Leu Val Leu 125         (1)        140                155                  170
CCT GCT GCC TTC CCT GCC CCA GTA CCC CCA GGA GAA GAT TCC AAA GAT GTA GCC
Pro Ala Ala Phe Pro Ala Pro Val Pro Pro Gly Glu Asp Ser Lys Asp Val Ala 185                200                  215
GCC CCA CAC AGA CAG CCA CTC ACC TCT TCA GAA CGA ATT GAC AAA CAA ATT CGG
Ala Pro His Arg Gln Pro Leu Thr Ser Ser Glu Arg Ile Asp Lys Gln Ile Arg 230                245                260                275
TAC ATC CTC GAC GGC ATC TCA GCC CTG AGA AAG GAG ACA TGT AAC AAG AGT AAC
Tyr Ile Leu Asp Gly Ile Ser Ala Leu Arg Lys Glu Thr Cys Asn Lys Ser Asn 290                305                320
ATG TGT GAA AGC AGC AAA GAG GCA CTG GCA GAA AAC AAC CTG AAC CTT CCA AAG
MET Cys Glu Ser Ser Lys Glu Ala Leu Ala Glu Asn Asn Leu Asn Leu Pro Lys 335                350                365                380
ATG GCT GAA AAA GAT GGA TGC TTC CAA TCT GGA TTC AAT GAG GAG ACT TGC CTG
MET Ala Glu Lys Asp Gly Cys Phe Gln Ser Gly Phe Asn Glu Glu Thr Cys Leu 395                410                425                440
GTG AAA ATC ATC ACT GGT CTT TTG GAG TTT GAG GTA TAC CTA GAG TAC CTC CAG
Val Lys Ile Ile Thr Gly Leu Leu Glu Phe Glu Val Tyr Leu Glu Tyr Leu Gln 455                470                485
AAC AGA TTT GAG AGT AGT GAG GAA CAA GCC AGA GCT GTG CAG ATG AGT ACA AAA
Asn Arg Phe Glu Ser Ser Glu Glu Gln Ala Arg Ala Val Gln MET Ser Thr Lys 500                515                530                545
GTC CTG ATC CAG TTC CTG CAG AAA AAG GCA AAG AAT CTA GAT GCA ATA ACC ACC
Val Leu Ile Gln Phe Leu Gln Lys Lys Ala Lys Asn Leu Asp Ala Ile Thr Thr 560                575                590
CCT GAC CCA ACC ACA AAT GCC AGC CTG CTG ACG AAG CTG CAG GCA CAG AAC CAG
Pro Asp Pro Thr Thr Asn Ala Ser Leu Leu Thr Lys Leu Gln Ala Gln Asn Gln 605                620                635                650
TGG CTG CAG GAC ATG ACA ACT CAT CTC ATT CTG CGC AGC TTT AAG GAG TTC CTG
Trp Leu Gln Asp MET Thr Thr His Leu Ile Leu Arg Ser Phe Lys Glu Phe Leu
```

FIGURE 3A

```
    665                    680              696        706         716
CAG TCC AGC CTG AGG GCT CTT CGG CAA ATG TAGCATGGGC ACCTCAGATT GTTGTTGTTA
Gln Ser Ser Leu Arg Ala Leu Arg Gln MET 726        736        746        756        766        776        786
ATGGGCATTC CTTCTTCTGG TCAGAAACCT GTCCACTGGG CACAGAACTT ATGTTGTTCT CTATGGAGAA 796        806        816        826        836        846        856
CTAAAAGTAT GAGCGTTAGG ACACTATTTT AATTATTTTT AATTTATTAA TATTTAAATA TGTGAAGCTG 866        876        886        896        906        916        926
AGTTAATTTA TGTAAGTCAT ATTTATATTT TTAAGAAGTA CCACTTGAAA CATTTTATGT ATTAGTTTTG 936        946        956        966        976        986        996
AAATAATAAT GGAAAGTGGC TATGCAGTTT GAATATCCTT TGTTTCAGAG CCAGATCATT TCTTGGAAAG 1006       1016       1026       1036       1046       1056       1066
TGTAGGCTTA CCTCAAATAA ATGGCTAACT TATACATATT TTTAAAGAAA TATTTATATT GTATTTATAT 1076       1086       1096       1106       1116       1126       1136
AATGTATAAA TGGTTTTTAT ACCAATAAAT GGCATTTTAA AAAATTCAAA AAAAAAAAAA AAAAAAGAA

TTC
```

FIGURE 4

```
1                                           10
ACC CCC CTG GGC CCT GCC AGC TCC CTG CCC CAG AGC TTC CTG CTC
Thr Pro Leu Gly Pro Ala Ser Ser Leu Pro Gln Ser Phe Leu Leu 20                                      30
AAG TGC TTA GAG CAA GTG AGG AAG ATC CAG GGC GAT GGC GCA GCG
Lys Cys Leu Glu Gln Val Arg Lys Ile Gln Gly Asp Gly Ala Ala

40
CTC CAG GAG AAG CTG TGT GCC ACC TAC AAG CTG TGC CAC CCC GAG
Leu Gln Glu Lys Leu Cys Ala Thr Tyr Lys Leu Cys His Pro Glu 50                                      60
GAG CTG GTG CTG CTC GGA CAC TCT CTG GGC ATC CCC TGG GCT CCC
Glu Leu Val Leu Leu Gly His Ser Leu Gly Ile Pro Trp Ala Pro

70
CTG AGC AGC TGC CCC AGC CAG GCC CTG CAG CTG GCA GGC TGC TTG
Leu Ser Ser Cys Pro Ser Gln Ala Leu Gln Leu Ala Gly Cys Leu 80                                      90
AGC CAA CTC CAT AGC GGC CTT TTC CTC TAC CAG GGG CTC CTG CAG
Ser Gln Leu His Ser Gly Leu Phe Leu Tyr Gln Gly Leu Leu Gln

100
GCC CTG GAA GGG ATC TCC CCC GAG TTG GGT CCC ACC TTG GAC ACA
Ala Leu Glu Gly Ile Ser Pro Glu Leu Gly Pro Thr Leu Asp Thr 110                                     120
CTG CAG CTG GAC GTC GCC GAC TTT GCC ACC ACC ATC TGG CAG CAG
Leu Gln Leu Asp Val Ala Asp Phe Ala Thr Thr Ile Trp Gln Gln

130
ATG GAA GAA CTG GGA ATG GCC CCT GCC CTG CAG CCC ACC CAG GGT
Met Glu Glu Leu Gly Met Ala Pro Ala Leu Gln Pro Thr Gln Gly 140                                     150
GCC ATG CCG GCC TTC GCC TCT GCT TTC CAG CGC CGG GCA GGA GGG
Ala Met Pro Ala Phe Ala Ser Ala Phe Gln Arg Arg Ala Gly Gly

160
GTC CTG GTT GCC TCC CAT CTG CAG AGC TTC CTG GAG GTG TCG TAC
Val Leu Val Ala Ser His Leu Gln Ser Phe Leu Glu Val Ser Tyr 170     174
CGC GTT CTA CGC CAC CTT GCC CAG CCC T
Arg Val Leu Arg His Leu Ala Gln Pro
```

FIGURE 5

```
                ***
1.  5'  AATTCGCCGCCACCATGTACAGGATGCAACTCCTGTCTTGCATTGCACTAAGTCTTGCA
2.  5'  GACAAGTGCAAGACTTAGTGCAATGCAAGACAGGAGTTGCATCCTGTACATGGTGGCGGCG
3.  5'  CTTGTCACAAACAGTGCACCTACTAGCTCGAGTACAAGAAGAACACAGCTACAACTGGAG
4.  5'  TAAATGCTCCAGTTGTAGCTGTGTTCTTCTTGTACTCGAGCTAGTAGGTGCACTGTTTGT
5.  5'. CATTTACTTCTGGATCTGCAGATGATTTCGAATGGAATTAATAATTACAGAAATCCTAGG
6.  5'  GGTGAGCCTAGGATTTCTGTAATTATTAATTCCATTCGAAATCATCTGCAGATCCAGAAG
7.  5'  CTCACCAGGATGCTCACATTCAGATTCTACATGCCCAGAAAGGCCACAGAACTGAGACAT
8.  5'  CTGAAGATGTCTCAGTTCTGTGGCTCTTCTGGGCATGTAGAATCTGAATGTGAGCATCCT
9.  5'  CTTCAGTGTCTAGAAGAAGAACTCAGACCTCTGGAGGAAGTGCTAAATTTAGCTCAAAGC
10. 5'  GTTCTTGCTTTGAGCTAAATTTAGCACTTCCTCCAGAGGTCTGAGTTCTTCTTCTAGACA
11. 5'  AAGAACTTTCACTTAAGACCCCGGGACTTAATCAGCAATATCAACGTAATAGTTCTGGAA
12. 5'  TCTTAGTTCCAGAACTATTACGTTGATATTGCTGATTAAGTCCCGGGGTCTTAAGTGAAA
13. 5'  CTAAGAGGATCCGAAACAACATTCATGTGTGAATATGCTGATGAGACAGCAACCATTGTA
14. 5'  GAATTCTACAATGGTTGCTGTCTCATCAGCATATTCACACATGAATGTTGTTTCGGATCC
15. 5'  GAATTCCTGAACAGATGGATTACCTTTGCTCAAAGCATCATCTCAACACTGACTTGATAAC
16. 5'  TCGAGTTATCAAGTCAGTGTTGAGATGATGCTTTGAGCAAAGGTAATCCATCTGTTCAG
```

FIGURE 5A

```
       ***
1. 5'  AATTCGCCGCCACCATGTACAGGATGCAACTCCTGTCTTGCATTGCACTAAGTCTTGCA
2. 5'  GACAAGTGCAAGACTTAGTGCAATGCAAGACAGGAGTTGCATCCTGTACATGGTGGCGGCG
3. 5'  CTTGTCACAAACAGTGCACCTACTAGCTCGAGTACAAGAAGAACACAGCTACAACTGGAG
4. 5'  TAAATGCTCCAGTTGTAGCTGTGTTCTTCTTGTACTCGAGCTAGTAGGTGCACTGTTTGT
5. 5'  CATTTACTTCTGGATCTGCAGATGATTTCGAATGGAATTAATAATTACAGAAATCCTAGG
6. 5'  GGTGAGCCTAGGATTTCTGTAATTATTAATTCCATTCGAAATCATCTGCAGATCCAGAAG
7. 5'  CTCACCAGGATGCTCACATTCAGATTCTACATGCCCAGAAAGGCCACAGAACTGAGACAT
8. 5'  CTGAAGATGTCTCAGTTCTGTGGCTCTTCTGGGCATGTAGAATCTGAATGTGAGCATCCT
9. 5'  CTTCAGTGTCTAGAAGAAGAACTCAGACCTCTGGAGGAAGTGCTAAATTTAGCTCAAAGC
10.5'  GTTCTTGCTTTGAGCTAAATTTAGCACTTCCTCCAGAGGTCTGAGTTCTTCTTCTAGACA
11.5'  AAGAACTTTCACTTAAGACCCCGGGACTTAATCAGCAATATCAACGTAATAGTTCTGGAA
12.5'  TCTTAGTTCCAGAACTATTACGTTGATATTGCTGATTAAGTCCCGGGGTCTTAAGTGAAA
13.5'  CTAAGAGGATCCGAAACAACATTCATGTGTGAATATGCTGATGAGACAGCAACCATTGTA
14.5'  GAATTCTACAATGGTTGCTGTCTCATCAGCATATTCACACATGAATGTTGTTTCGGATCC
15.5'  GAATTCCTGAACAGATGGATTACCTTTTGTCAAAGCATCATCTCAACACTGACTTGATAAC
16.5'  TCGAGTTATCAAGTCAGTGTTGAGATGATGCTTTGAGCAAAGGTAATCCATCTGTTCAG
```

SITE-SPECIFIC HOMOGENEOUS MODIFICATION OF POLYPEPTIDES

The present invention relates generally to polypeptides modified by the attachment thereto of compounds having amine reactive groups, methods for producing such modified polypeptides and compositions containing the modified polypeptides. More particularly, the invention relates to homogeneous modified polypeptides which are modified by attachment of hydrophilic moieties, including polymers, to selected positions in the polypeptide.

BACKGROUND

The desirability of modifying biologically active and therapeutically useful polypeptides with a variety of compounds having amine reactive groups, such as hydrophilic polymers, e.g., polyethylene glycol (PEG), to enhance their pharmacokinetic properties has been noted. See, e.g., the discussion of the art in this area of polypeptide modification in published PCT patent application No. WO87/00056. Such modification has been attempted to reduce adverse immune response to the polypeptide, increase the solubility for use in pharmaceutical preparations, and maintain a desirable circulatory level of such polypeptide for therapeutic efficacy.

One significant problem not addressed by the extensive art in this area of polypeptide modification involves the extent to which a polypeptide can be modified by attachment of compounds having amine reactive groups. For example, treatment of a polypeptide with PEG or similar polymers, can result in random attachment of the polymer at the amino terminus of the polypeptide and/or at one or more lysine residues in the amino acid sequence of the protein. While several PEG groups can attach to the polypeptide, the end result is a composition containing or potentially containing a variety of species of "PEG-ylated" polypeptide. Such heterogeneieity in composition is undesirable for pharmaceutical use.

The attachment of compounds with amine reactive groups to a polypeptide may alter the biological activity of the polypeptide. This effect is believed mediated by the position and number of the attachment site(s) along the polypeptide sequence. There thus remains in the art a need for a method enabling site specific attachment of such compounds to polypeptides, in a manner that enables the manipulation of the number and position of attachment sites. Such site specific attachments can generate homogeneously modified polypeptides which are therapeutically efficacious and which retain certain desirable characteristics of the natural polypeptides.

SUMMARY OF THE INVENTION

This invention provides materials and methods for site specific covalent modification of polypeptides permitting the production of compositions comprising homogeneously modified polypeptides or proteins and pharmaceutical compositions containing same. "Homogeneous modified" as the term is used herein means substantially consistently modified only at specific lysine residues. A homogeneously modified G-CSF, for example, includes a G-CSF composition which is substantially consistently modified at position 40, but not at positions 16, 23 and 34.

To solve the problem of non-specific susceptibility of polypeptides to covalent modification by amine-reactive moieties, this invention first provides lysine-depleted variants ("LDVs") of polypeptides of interest. LDVs of this invention encompass polypeptides and proteins which contain fewer reactive lysine residues than the corresponding naturally occurring or previously known polypeptides or proteins. The lysine residues in the peptide structure of the LDVs may occur at one or more amino acid positions occupied by lysine residues in the natural or previously known counterpart, or may be located at positions occupied by different amino acids in the parental counterpart. Furthermore, LDVs may in certain cases contain more lysine residues than the parental counterpart, so long as the number of lysine residues in the LDV permits homogeneous modification by reaction of the LDVs with amine-reactive moieties, as discussed below. Since such polypeptides or proteins of this invention contain a small number of lysine residues, generally six or less, preferably 1−∼4 lysines, they are also referred to herein as "LDVs" even though containing more lysine residues than the parental counterpart.

Polypeptides of interest include both proteins and polypeptides useful in therapeutic, prophylactic and/or diagnostic applications, including hematopoietins such as colony stimulating factors, e.g. G-CSF, GM-CSF, M-CSF, CSF-1, Meg-CSF, erythropoietin (EPO), IL-1, IL-2, IL-3, IL-4, IL-5, IL-6, B-cell growth factor, B-cell differentiation factor, eosinophil differentiation factor, erythroid potentiating activity (EPA), macrophage activating factor, interferons and tumor necrosis factor, among others; thrombolytic agents such as tPA, urokinase (uPA) and streptokinase and variants thereof as are known in the art; proteins involved in coagulation and hemostasis, including Factor V, Factor VII, Factor VIII, Factor IX, Factor XIII, Protein C and Protein S; proteins and polypeptides useful as vaccines; as well as other proteins and polypeptides and analogs thereof, including for example superoxide dismutase (SOD)(including extracellular SOD); growth hormones such as human and bovine growth hormone, epidermal growth factor, fibroblast growth factor, transforming growth factors TGFα and TGFβ, insulin-like growth factor, PDGF, and ODGF; pulmonary surfactant proteins (PSPs); calcitonin; somatostatin; catalase; elastase; inhibins; angiogenic factors; atrial natriuretic factor; FSH, LH, FSH-releasing hormone, LH-releasing hormone and HCG; immunotoxins and immunoconjugates; and anti-thrombin III; and bone or cartilage morphogenic factors. In order to provide additional disclosure concerning exemplary proteins mentioned above and their uses, the following published foreign applications and co-owned pending U.S. applications are hereby incorporated by reference herein: PCT Nos. WO 86/00639 and WO 85/05124; and U.S. Ser. Nos. 940,362; 047,957; 021,865; and 099,938. Sequence information for other proteins mentioned above are also known in the art.

Most proteins and polypeptides contain several lysine residues within their peptide structure. By "lysine depleted variant" as the term is used herein, I mean variants of proteins or polypeptides which are modified in amino acid structure relative to naturally occurring or previously known counterparts in one or both of the following respects:

(i) at least one lysine residue of the natural or previously known compound is deleted or replaced with a substitute amino acid, preferably arginine;

(ii) at least one lysine residue is inserted into the natural or previously known sequence and/or is used to replace a different amino acid within that sequence.

With respect to modification (i), above, it is typically preferred in the case of lymphokines and other proteins of like molecular size that all but 1–~6 of the original lysines be deleted and/or replaced. In general, for consistent homogeneous modification of the LDVs the fewer lysines remaining in the LDV the better, e.g. only 1–~4 lysines. It should be understood, however, that in certain cases LDVs containing more than 4–~6 reactive lysines may, given appropriate location and spacing of such lysines, be capable of homogeneous modification, e.g. PEGylation, and upon such modification may possess advantageous biological properties such as differential binding to receptors, antibodies or inhibitors relative to the parental protein, as discussed below. It should also be understood that in accordance with modification (ii), above, one or more additional lysine residues may be inserted into the natural or previously known sequence and/or used to replace as desired other amino acids therein, e.g. arginine. Thus all lysines may be deleted or replaced in accordance with (i), and one or more new lysines may be inserted or used to replace a different amino acid in the molecule. Alternatively, all but one or two, for example, of the lysines in the natural or previously known sequence may be deleted or replaced with other amino acids, e.g. arginine. In any event, and as described in greater detail below, the LDVs of this invention make it possible for the first time to produce homogeneous compositions containing polypeptides or proteins (LDVs) substantially specifically and consistently modified at selected positions using amine-reactive moieties (described hereinafter) as the modifying agents.

Thus, in the practice of this invention, lysine residues are identified in those portions of the polypeptide where modification via amino-reactive moieties is not desired. The lysine residues so identified are deleted or replaced with different amino acids, e.g. by genetic engineering methods as described below. Preferably replacements are conservative, i.e. lysine is replaced by arginine, and where a new lysine is to be introduced, arginine by lysine. Any remaining lysine residues represent sites where modification by amine-reactive moieties is desired. Alternatively, or in addition, novel lysine residues may be engineered into the polypeptide at positions where attachment is desired, most conveniently, for example, by simple insertion of a lysine codon into the DNA molecule at the desired site or by converting a desirably located arginine or other codon to a lysine codon. Convenient methods for (i) site specific mutagenesis or DNA synthesis for producing a DNA molecule encoding the desired LDV, (ii) expression in procaryotic or eucaryotic host cells of the DNA molecule so produced, and (iii) recovery of the LDV produced by such expression are also disclosed in detail below.

The LDVs of this invention retain useful biological properties of the natural or previously known polypeptide or protein, and may thus be used, with or without modification with amine-reactive moieties, for applications identified for the non-modified parent polypeptide or protein. Modification with such moieties, however, is preferred. Such modified LDVs are producable in homogeneous compositions which, it is contemplated, will provide improved pharmacokinetic profiles and/or solubility characteristics relative to the parent polypeptides.

In cases where the parental polypeptide normally can interact with one or more receptors, as in the case of IL-2 for example, it is contemplated that modified LDVs of the polypeptide wherein the modification masks one or more receptor binding sites may interact e.g. with only one type of its receptors, i.e. not interact with one or more other types of receptors which interact with the parental polypeptide. Such modified LDVs may represent therapeutic agents having more specific biological and pharmacologic activities than the corresponding parental polypeptide. In cases where the parental polypeptide normally can interact with an inhibitor, as in the case of tPA, it is contemplated that modified LDVs of such polypeptides or proteins wherein the modification masks an inhibitor binding site may have a reduced or substantially abolished interaction with the inhibitor, and thus improved utility as a therapeutic agent. In cases where the natural or recombinant protein can elicit neutralizing or otherwise inhibitory antibodies in humans, as in the case of Factor VIII, modified LDVs wherein the modification masks the epitope for such antibodies may represent the first potential therapeutic, and indeed, life saving, agents. Finally, where specific proteolytic cleavage inactivates or otherwise negatively affects therapeutic utility of a protein, as in the case of the APC cleavage site in Factor VIII or the proteolytic cleavage site in prourokinase which liberates the kringle region from the serine protease domain, modified LDVs of the protein wherein the modification masks the cleavage site may represent potential therapeutic agents with longer effective in vivo half life or other improved properties relative to the parental protein.

Biological activity of the LDVs before or after modification with the amine-reactive moieties may be determined by standard in vitro or in vivo assays conventional for measuring activity of the parent polypeptide.

Selective and homogeneous modification of the LDVs with amine-reactive moieties is possible since such moieties will covalently bond only to ε-amino groups of the remaining lysine residue(s) in the LDVs and to the amino terminus of the LDV, if reactive. The modified LDVs so produced may then be recovered, and if desired, further purified and formulated with into pharmaceutical compositions by conventional methods.

It is contemplated that certain polypeptides or proteins may contain one or more lysine residues, which by virtue of peptide folding or glycosylation, for example, are not accesible to reaction with amine-reactive moieties, except under denaturing conditions. In the practice of this invention such non-reactive lysine residues may be, but need not be, altered since they will not normally be susceptible to non-specific modification by amine-reactive moieties. The presence in parental polypeptides or proteins of non-reactive lysine residues may be conveniently determined, if desired, by modifying the parental polypeptide or protein with an amine-reactive compound which results in the attachment to reactive lysines of a modifying moiety of known molecular weight under denaturing and non-denaturing conditions, respectively, and determining, e.g. by SDS-PAGE analysis, the number of attached moieties in each case. The presence and number of additional attached moieties on the denatured parental polypeptide relative to the non-denatured parental polypeptide is a general indication of the presence and number of non-reactive lysine residues. The locations of any such non-reactive lysine residues may be determined, e.g. by SDS-PAGE analysis of proteolytic fragments of the polypeptide modified under denaturing and non-denaturing conditions. Lysine residues which are modified sometimes but not always under the reaction conditions selected for the practice of this invention are deemed reactive lysine residues for the purpose of this disclosure.

Amine-reactive moieties include compounds such as succinic anyhydride and polyalkylene glycols, e.g. polyethylene and polypropylene glycols, as well as derivatives thereof, with or without coupling agents or derivatization with coupling moieties, e.g. as disclosed in U.S. Pat. No. 4,179,337; published European Patent Application No. 0 154 316; published International Application No. WO 87/00056; and Abuchowski and Davis, in "Enzymes as Drugs" (1981), Hokenberg & Roberts, eds. (John Wiley & Sons, N.Y.), pp. 367–383.

Generally, the method for modifying the LDVs can be depicted as follows:

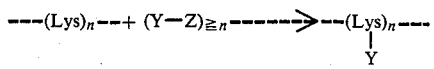

wherein "-----" represents the polypeptide backbone of the LDV, "Lys" represents a reactive lysine residue within the polypeptide sequence, "Y–Z" represents the amine-reactive moiety, "Y" represents a hydrophilic moiety which becomes covalently linked to the ε-amino group of the lysine residue(s) in the course of the depicted reaction; and "n" is an integer.

Briefly, the method comprises reacting the LDV with an amine reactive compound under suitable conditions, preferably non-denaturing conditions, and in sufficient amounts permitting the covalent attachment of the hydrophilic moiety to lysine residue(s) present in the polypeptide backbone of the LDV. Generally, the amount of amine-reactive compound used should be at least equimolar to the number of lysines to be derivatized, although use of excess amine-reactive compound is strongly preferred, both to improve the rate of reaction and to insure consistent modification at all reactive sites. The modified LDV so produced, may then be recovered, purified and formulated by conventional methods. See e.g., WO 87/00056 and references cited therein.

While any polypeptide is a candidate for the method of the invention, presently desirable polypeptides to be homogeneously modified include lymphokines and growth factors. Of significant interest are those polypeptides which affect the immune system, including the colony stimulating factors, and other growth factors.

Other aspects of the present invention include therapeutic methods of treatment and therapeutic compositions which employ the modified polypeptide LDVs of the present invention. These methods and compositions take advantage of the improved pharmacokinetic properties of these modified LDVs to provide treatments, e.g., such as employing lower dosages of polypeptide, less frequent administration, and more desirable distribution, required for the therapeutic indications for the natural polypeptide.

Other aspects and advantages of the present invention will be apparent upon consideration of the following detailed description of the invention, including illustrative examples of the practice thereof.

BRIEF DESCRIPTION OF THE DRAWINGS

FIG. 1 is the polypeptide sequence of IL-2, with amino acid numbers used for reference in the specification.

FIG. 2 is the polypeptide sequence of IL-3, with amino acid numbers used for reference in the specification.

FIG. 3 is the polypeptide sequence of IL-6, with amino acid numbers used for reference in the specification.

FIG. 4 is the polypeptide sequence of G-CSF, with amino acid numbers used for reference in the specification.

FIG. 5 illustrates synthetic oligonucleotides for the preparation of synthetic DNA molecules encoding exemplary IL-2 LDVs of the invention; odd numbered oligonucleotides correspond to sequences within sense strands, even numbered oligonucleotides to anti-sense strands; the initiation ATG is marked with "***" and altered codons are underlined; oligonucleotides in FIG. 5A yield the LDV with alanine at position 125 and oligonucleotides in FIG. 5B yield the LDV with cystein at position 125.

DETAILED DESCRIPTION OF THE INVENTION

The present invention involves the selective modification of polypeptides of interest for pharmaceutical use, to both enhance their pharmacokinetic properties and provide homogeneous compositions for human therapeutic use. Any polypeptide is susceptible to use in the method of the invention. Most desirably, a polypeptide having one or more lysine residues in its amino acid sequence, where it would be desirable to attach an amine reactive compound, may be employed. Also polypeptides having arginine residues which may be converted to lysine residues for such attachments may be employed. Finally, lysine residues may be inserted into a sequence which has no conveniently located lysine or arginine residues.

The method for selectively modifying the polypeptide of choice involves selecting locations in the polypeptide sequence for the attachment of amine reactive compounds. This step may be accomplished by altering the amino acid sequence of the polypeptide by converting selected lysine residues into arginine residues, or converting selected arginine residues into lysine residues. For example, the codons AAA or AAG, which code for lysine, can be changed to the codons AGA, AGG, CGA, CGT, CGC, or CGG which code for arginine, and vice versa. Alternatively, lysine residues may be inserted into and/or deleted from a peptide sequence at a selected site(s).

LDVs in accordance with this invention also include proteins with allelic variations, i.e. sequence variations due to natural variability from individual to individual, or with other amino acid substitutions or deletions which still retain desirable biological properties of the parental protein or polypeptide.

All LDVs of this invention may be prepared by expressing recombinant DNA sequences encoding the desired variant in host cells, e.g. procaryotic host cells such as E. coli, or eucaryotic host cells such as yeast or mammalian host cells, using methods and materials, e.g. vectors, as are known in the art. DNA sequences encoding the variants may be produced synthetically or by conventional site-directed mutagenesis of DNA sequences encoding the protein or polypeptide of interest or analogs thereof.

DNA sequences encoding various proteins of interest have been cloned and the DNA sequences published. DNA sequences encoding certain proteins of interest have been deposited with the American Type Culture Collection (See Table 1). DNA molecules encoding a protein of interest may be obtained (i) by cloning in accordance with published methods, (ii) from deposited plasmids, or (iii) by synthesis, e.g. using overlapping synthetic oligonucleotides based on published sequences which together span the desired coding region.

As mentioned above, DNA sequences encoding individual LDVs of this invention may be produced synthetically or by conventional site-directed mutagenesis of a DNA sequence encoding the parental protein or polypeptide of interest or analogs thereof. Such methods of mutagenesis include the M13 system of Zoller and Smith, Nucleic Acids Res. 10:6487–6500 (1982); Methods Enzymol. 100:468–500 (1983); and DNA 3:479–488 (1984), using single stranded DNA and the method of Morinaga et al., Bio/technology, 636–639 (July 1984), using heteroduplexed DNA. Exemplary oligonucleotides used in accordance with such methods are described below. It should be understood, of course, that DNA encoding each of the LDVs of this invention may be analogously produced by one skilled in the art through site-directed mutagenesis using appropriately chosen oligonucleotides.

The new DNA sequences encoding the LDVs of this invention can be introduced into appropriate vectors for expression in the desired host cells, whether procaryotic or eucaryotic. The activity produced by the transiently transfected or stably transformed host cells may be measured by using standard assays conventional for the parental protein.

The LDV produced by expression in the genetically engineered host cells may then be purified, and if desired formulated into pharmaceutical compositions by conventional methods, often preferably by methods which are typically used in purifying and/or formulating the parental protein. It is contemplated that such pharmaceutical compositions containing the LDV in admixture with a pharmaceutically acceptable carrier will possess similar utilities to those of the parental proteins.

In another, and preferred, aspect of this invention, the LDVs produced by recombinant means as mentioned above are reacted with the desired amine-reactive compound under conditions permitting attachment of the compound to the $\epsilon$-amino groups at remaining lysine residues in the peptide backbone of the LDV.

The term "amine reactive compound" is defined herein as any compound having a reactive group capable of forming a covalent attachment to the Epsilon amine group of a lysine residue. Included among such compounds are hydrophilic polymers such as PEG and polypropylene glycol (PPG); compounds such as succinic anhydride; and others. Methods for such attachment are conventional, such as described in PCT application No. WO97/00056 and references described therein. However, by controlling the number and location of the remaining lysines in the LDV sequence, the number and location(s) of the attached moiety can be selectively controlled. Such control of attachment location and number enables the production of only certain selectively modified molecules retaining the desired biological activity, rather than production of a heterogeneous mixture of variably modified molecules, only some of which may be active.

Another aspect of the invention is therefore homogeneous compositions of modified LDVs as described herein, e.g. PEGylated LDVs. Specific embodiments of polypeptide LDVs of the invention include IL-2 which has arginine residues replacing lysine residues at one or more of the lysine residues at positions 8, 9, 32, 35, 43, 48, 49, 54, 64, 76, and 97. A presently desirable example of such a modified IL-2 has the natural lysine residue only at position 76, with all other lysine residue positions as identified above being replaced by arginine residues and with lysine 76 being coupled to PEG.

TABLE 1

| protein | DNA encoding exemplary proteins of interest vector & ATCC accession # | references |
|---|---|---|
| G-CSF | pxMT2G-CSF (67514) | (1) |
| GM-CSF | pCSF-1 ( ) | (2) |
| M-CSF | p3ACSF-69 (67092) | (3) |
| CSF-1 | | (4) |
| IL-2 | pBR322-aTCGF (39673) | (6) |
| IL-3 | pCSF-MLA (67154); CSF-16 (40246); pHuIL3-2 (67319); pSHIL-3-1 (67326) | (7) |
| IL-6 | pCSF309 (67153); pAL181(40134) | (8) |
| tPA | pIVPA/1 (39891); J205 (39568) | (9) |
| FVIII | pSP64-VIII (39812); pDGR-2 (53100) | (10) |
| ATIII | p91023 AT III-C3 (39941) | (11) |
| SOD | | (12) |

1 U.S. Ser. No. 099,938 and references cited therein; published PCT WO 87/01132.
2 WO 86/00639; Wong et al., Science
3 WO 87/06954
4 Kawasaki et al., 1985, Science 230:291–296
6 U.S. Ser. No. 849,234 (filed April 6, 1986)
7 PCT/US87/01702
8 PCT/US87/01611
9 WO 87/04722; U.S. Ser. Nos. 861,699; 853,781; 825,104; and 882, 051; U.S. Ser. No. 566,057; D. Pennica et al., 1983, Nature 301:214; Kaufman et al., 1985, Mol. Cell. Biol. 5(7):1750 et seq.
10 GI 5002; WO 87/07144
11 U.S. Ser. Nos. 677,813; 726,346; and 108,878; U.S. Pat. No. 4,632,981
12 WO 87/01387

Amino acid numbers correlate with the numbering system used in FIG. 1 for the appropriate unmodified peptides.

Similarly, one or more of the naturally occurring lysine residues in IL-3 (FIG. 2) at amino acid positions 10, 28, 66, 79, 100, 110 and 116 may be converted to a suitable amino acid, such as arginine, to create a polypeptide LDV of the invention. For example, one such polypeptide has positions 10, 28, 100, 110 and 116 converted to arginine and the remaining lysine residues at positions at 79 and 66 coupled to PPG. Alternatively one or more of the arginine residues may be converted to lysine residues. Table 2 below illustrates the positions and amino acid numbers of lysine and arginine residues in several exemplary polypeptides which can be altered according to the invention. The position numbers correspond to the appropriate FIGS. 1 through 4.

Other modified peptides may be selected and produced in accordance with this invention as described for the above peptides, which are included as examples only.

Amine-reactive compounds will typically also react with the amino terminus of a polypeptide under the conditions described above, so long as the amino terminus is accessible to amine-reactive agents (i.e. reactive) and is not blocked. Therefore an alternatively modified polypeptide may be provided by blocking the reactive site on the amino terminus of the selected polypeptide LDV before reacting the LDV with the desired amine-reactive compound. Unblocking the N-terminus after the modifying moiety, e.g. polymer, has been covalently linked to LDV lysines will produce a modified polypeptide with polymer or other modifying moiety attached to the remaining lysines in the amino acid sequence of the LDV, but not at the amino terminus. Thus, compositions of polypeptides homogeneous for polymer attachment or lack of polymer attachment at the amino terminus are also encompassed by this invention.

LDVs of this invention, modified as described, encompass LDVs containing other modifications as well, including truncation of the peptide sequence, deletion or replacement of other amino acids, insertion of new N-linked glycosylation sites, abolishment of natural N-linked glycosylation sites, etc. Thus, this invention encompasses LDVs encoded for by DNA molecules which are capable of hybridizing under stringent conditions to the DNA molecule encoding the parental polypeptide or protein so long as one or more lysine residues of the parental peptide sequence is deleted or replace with a different amino acid and/or one or more lysine residues are inserted into the parental peptide sequence and the resulting LDV is covalently modified as described herein.

Because the method and compositions of this invention provide homogeneous modified polypeptides, the invention also encompasses such homogeneous compositions for pharmaceutical use which comprise a therapeutically effective amount of a modified LDV described above in a mixture with a pharmaceutically acceptable carrier. Such composition can be used in the same manner as that described for the natural or recombinant polypeptides. It is contemplated that the compositions will be used for treating a variety of conditions. For example, a modified IL-2 can be used to treat various cancers. A modified G-CSF can be used to treat neutropenia, e.g., associated with chemotherapy. The exact dosage and method of administration will be determined by the attending physician depending on the particular modified polypeptide employed, the potency and pharmacokinetic profile of the particular compound as well as on various factors which modify the actions of drugs, for example, body weight, sex, diet, time of administration, drug combination, reaction sensitivities and severity of the particular case. Generally, the daily regimen should be in the range of the dosage for the natural or recombinant unmodified polypeptide, e.g. for a colony stimulating factor such as G-CSF, a range of 1-100 micrograms of polypeptide per kilogram of body weight.

TABLE 2

| IL-2 residues | | IL-6 residues | |
| --- | --- | --- | --- |
| lysine | arginine | lysine | arginine |
| 8 | 38 | 10 | 17 |
| 9 | 81 | 28 | 25 |
| 32 | 83 | 42 | 31 |
| 35 | 120 | 47 | 41 |
| 43 | | 55 | 105 |
| 48 | | 67 | 114 |
| 49 | | 71 | 169 |
| 54 | | 87 | 180 |
| 64 | | 121 | 183 |
| 76 | | 129 | |
| 97 | | 130 | |
| | | 132 | |
| | | 151 | |
| | | 172 | |

| G-CSF residues | | IL-3 residues | |
| --- | --- | --- | --- |
| lysine | arginine | lysine | arginine |
| 16 | 22 | 10 | 54 |
| 23 | 146 | 28 | 55 |
| 34 | 147 | 66 | 63 |
| 40 | 166 | 79 | 94 |
| | 169 | 100 | 108 |
| | | 110 | 109 |
| | | 116 | |

The therapeutic method and compositions of the present invention may also include co-administration with other drugs or human factors. The dosage recited above would be adjusted to compensate for such additional components in the therapeutic composition or regimen. In the case of pharmaceutical compositions containing modified lymphokie LDVs, for example, progress of the treated patient can be monitored by periodic assessment of the hematological profile, e.g. white cell count and the like.

The following examples illustrate the method and compositions of the invention.

EXPERIMENTAL MATERIALS, METHODS AND EXAMPLES

Example 1: Eucaryotic Expression Materials and Methods

Eukaryotic cell expression vectors into which DNA sequences encoding LDVs of this invention may be inserted (with or without synthetic linkers, as required or desired) may be synthesized by techniques well known to those skilled in this art. The components of the vectors such as the bacterial replicons, selection genes, enhancers, promoters, and the like may be obtained from natural sources or synthesized by known procedures. See Kaufman et al., *J. Mol. Biol.*, 159:601–621 (1982); Kaufman, *Proc. Natl. Acad. Sci.* 82:689–693 (1985). See also WO 87/04187 (pMT2 and pMT2-ADA) and U.S. Ser. No. 88,188, filed Aug. 21, 1987)(pxMT2). Exemplary vectors useful for mammalian expression are also disclosed in the patent applications cited in Example 4, which are hereby incorporated by reference. Eucaryotic expression vectors useful in producing variants of this invention may also contain inducible promoters or comprise inducible expression systems as are known in the art. See U.S. Ser. No. 93,115 (filed Aug. 1, 1986) and PCT/US87/01871.

Established cell lines, including transformed cell lines, are suitable as hosts. Normal diploid cells, cell strains derived from in vitro culture of primary tissue, as well as primary explants (including relatively undifferentiated cells such as haematopoetic stem cells) are also suitable. Candidate cells need not be genotypically deficient in the selection gene so long as the selection gene is dominantly acting.

The host cells preferably will be established mammalian cell lines. For stable integration of the vector DNA into chromosmal DNA, and for subsequent amplification of the integrated vector DNA, both by conventional methods, CHO (Chinese Hamster Ovary) cells are presently preferred. Alternatively, the vector DNA may include all or part of the bovine papilloma virus genome (Lusky et al., Cell, 36: 391–401 (1984) and be carried in cell lines such as C127 mouse cells as a stable episomal element. Other usable mammalian cell lines include HeLa, COS-1 monkey cells, melanoma cell lines such as Bowes cells, mouse L-929 cells, 3T3 lines derived from Swiss, Balb-c or NIH mice, BHK or HaK hamster cell lines and the like.

Stable transformants then are screened for expression of the LDV product by standard immunological or activity assays. The presence of the DNA encoding the LDV proteins may be detected by standard procedures such as Southern blotting. Transient expression of the procoagulant genes during the several days after introduction of the expression vector DNA into suitable host cells such as COS-1 monkey cells is measured without selection by activity or immunologic assay of the proteins in the culture medium.

Following the expression of the DNA by conventional means, the variants so produced may be recovered, purified, and/or characterized with respect to physiochemical, biochemical and/or clinical parameters, all by known methods.

Example 2: Bacterial, Yeast and Insect Cell expression

Bacterial and yeast expression may be effected by inserting (with or without synthetic linkers, as required or desired) the DNA molecule encoding the desired LDV into a suitable vector (or inserting the parental DNA sequence into the vector and mutagenizing the sequence as desired therein) and transforming the host cells with the vector so produced using conventional vectors and methods as are known in the art, e.g. as disclosed in published PCT Application No. WO 86/00639. Transformants are identified by conventional methods and may be subcloned if desired. Characterization of transformants and recombinant product so produced may be effected and the product recovered and purified, all as described in Example 1.

For bacterial expression, the DNA sequences encoding the LDVs are preferably modified by conventional procedures to encode only the mature polypeptide and may optionally be modified to include preferred bacterial codons.

Example 3: Insect Cell Expression

Similarly, expression of the recombinant LDVs may be effected in insect cells, e.g. using the methods and materials disclosed therefor in published European Applications Nos. 0 155 476 A1 or 0 127 839 A2 and in Miller et al., *Genetic Engineering,* Vol.8, pp.277-298 (J. K. Setlow and A. Hollander, eds., Plenum Press, 1986); Pennock et al., 1984, Mol. Cell. Biol. 4:(3)399-406; or Maeda et al., 1985, Nature 315:592-594.

Example 4: Mutagenesis Protocol

Site directed mutagenesis may be effected using conventional procedures known in the art. See e.g. published International Applications Nos. WO 87/07144 and WO 87/04722 and U.S. Ser. Nos. 099,938 (filed Sept. 23, 1987) and 088,188 (filed Aug. 21, 1987) and the references cited therein.

Example 5: Exemplary Oligonucleotides for Mutagenesis Reactions

The following oligonucleotides were designed for the indicated exemplary mutagenesis reactions:

| # | sequence | modification |
|---|---|---|
| | | [IL-2 K >R at position:] |
| 1 | CA AGT TCT ACA AGG AAA ACA CAG C | 8 |
| 2 | GT TCT ACA AAG AGA ACA CAG CTA C | 9 |
| 3 | GGA AAT AAT TAC AGG AAT CCC AAA C | 32 |
| 4 | C AAG AAT CCC AGA CTC ACC AGG ATG C | 35 |
| 5 | G CTC ACA TTT AGG TTT TAC ATG CCC | 43 |
| 6 | G TTT TAC ATG CCC AGG AAG GCC ACA GAA C | 48 |
| 7 | G TTT TAC ATG CCC AAG AGG GCC ACA GAA C | 49 |
| 8 | GCC ACA GAA CTG AGA CAT CTT CAG TG | 54 |
| 9 | GAA GAA GAA CTC AGA CCT CTG GAG G | 64 |
| 10 | GCT CAA AGC AGA AAC TTT CAC TTA AG | 76 |
| 11 | GTT CTG GAA CTA AGG GGA TAT GAA AC | 97 |
| | | R >K at position: |
| 12 | CCC AAA CTC ACC AAG ATG CTC ACA TTT | 38 |
| 13 | C TTT CAC TTA AAA CCC AGG GAC | 81 |
| 14 | CAC TTA AGA CCC AAG GAC TTA ATC AGC | 83 |
| 15 | GAA TTT CTG AAC AAA TGG ATT ACC TTT TG | 120 |
| | | [G-CSF K >R at position:] |
| 16 | GC TTC CTG CTC AGG TGC TTA GAG C | 16 |
| 17 | G CAA GTG AGG AGG ATC CAG GGC G | 23 |
| 18 | GCG CTC CAG GAG AGG CTG TGT GCC ACC | 34 |
| 19 | GT GCC ACC TAC AGG CTG TGC CAC CCC | 40 |
| | | R >K at position:] |
| 20 | GC TTA GAG CAA GTG AAG AAG ATC CAG GGC | 22 |
| 21 | CT GCT TTC CAG AAA CGG GCA GGA GGG | 146 |
| 22 | GCT TTC CAG CGC AAG GCA GGA GGG GTC C | 147 |
| 23 | GAG GTG TCG TAC AAG GTT CTA CGC CAC C | 166 |
| 24 | C CGC GTT CTA AAG CAC CTT GCC CAG CCC | 169 |

In the exemplary oligonucleotides depicted above regions designed to effect a codon alteration are underlined. It should be understood of course that the depicted list of oligonucleotides is merely exemplary and not exclusive. The design and synthesis of alternative and additional oligonucleotides for mutagenesis in accord with this invention is well within the present skill in the art given the benefit of this disclosure.

Synthesis of such oligonucleotides may be conveniently effected using conventional automated DNA synthesis equipment and methods, typically following the manufacturer's instructions.

One skilled in the art, of course, could readily design and synthesize other oligonucleotides for deletion of lysine codons or insertion thereof in DNA sequences encoding IL-2 or G-CSF. Additionally, one could also readily design and synthesize other oligonucleotides for similar mutagenesis of DNA encoding any desired protein or polypeptide for use in the production of LDVs of this invention. To modify more than one site mutagenesis may be carried out iteratively, or in some cases using an oligonucleotide designed for mutagenesis at more than one site. For example, to modify a DNA molecule encoding IL-2 to encode R-48, R-49 IL-2 one may mutagenize the parental DNA molecule iteratively using oligonucleotides 6 and 7, depicted above. Alternatively, one could mutagenize with the following oligonucleotide:

G CTC ACA TTT AAG TTT TAC ATG CCC <u>AGG AGG</u> GCC ACA GAA CTG AAA CAT CTT CAG which is designed to effect both mutagenesis reactions.

By way of example, one may readily produce a DNA molecule and express it to yield one of the following G-CSF LDVs:

Exemplary G-CSF LDVs

| | |
|---|---|
| 1. R-16 G-CSF | 9. R-23, R-40 G-CSF |
| 2. R-23 G-CSF | 10. R-34, R-40 G-CSF |
| 3. R-34 G-CSF | 11. R-16, R-23, R-34 G-CSF |
| 4. R-40 G-CSF | 12. R-16, R-34, R-40 G-CSF |
| 5. R-16, R-23 G-CSF | 13. R-23, R-34, R-40 G-CSF |
| 6. R-16, R-34 G-CSF | 14. K-169, R-16, R-23, R-34, R-40 G-CSF |
| 7. R-16, R-40 G-CSF | 15. R-16, R-34, K-147 G-CSF |
| 8. R-23, R-34 G-CSF | |

Modification by methods described herein of such G-CSF LDVs, for example, provides the following exemplary modified G-CSF LDVs:

[    K    R K    K K         R R    R R    ]

|
     |    R    R R    R R        R R    R R

|
     |         R R    R R        R R    R·R

|    |
     |    |    R    R R        R R    R R

|  |
     R    R R    |  |       R R    R R

|  |
     R    R R    R R       ·|  |    R R

|
     R    R R    R R        R R    | R

|
    ¯R    R R    R R        R R    R R |

|  |
     R    R R    R R        R R    R R    |  |

|
     R    R. R    R R        R R    R R       |

|    |                  |
     R    R |    R |       R |    R R wherein $$\Big|$$

represents a modification in accordance with this invention, e.g. PEGylation, at each reactive lysine residue in the LDV. The parental peptide sequence of G-CSF is depicted schematically at the top in brackets indicating the relative locations of positions 16, 23, 34 and 40 (occupied by lysine residues in G-CSF) and 22, 146, 166 and 169 (occupied by arginine residues in G-CSF). As depicted schematically above, all lysines not intended a potential attachment sites were replaced with arginine. It should be understood of course, that as previously mentions, lysines not intended as potential attachment sites may be replaced with other amino acids as well, or simply deleted, and one or more additional lysine residues may be added by insertion between or replacement of amino acid of the parental peptide sequence.

Example 6: Synthesis of DNA molecules encoding LDVs

As an alternative to the production of LDV-encoding DNA by mutagenesis of a parental DNA sequence, it should be understood that the desired LDV-encoding DNA may be prepared synthetically. In that case, it will usually be desirable to synthesize the DNA in the form of overlapping oligonucleotides, e.g. overlapping 50–80mers, which together span the desired coding sequence:

———————  ———————  ———————  ...

———————  ———————  ———————  ...

Given a desired coding sequence, the design, synthesis, assembly and ligation, if desired, to synthetic linkers of appropriate oligonucleotides is well within the present level of skill in the art.

Example 7: Preparation of PEG-vlated IL-2 LDV a. DNA Encoding the LDV

A DNA molecule encoding IL-2 containing arginine residues in place of lysine residues at positions 8, 9, 32, 35, 43, 48, 54, 64 and 97 (and alanine in place of cystein at position 125) is synthesized as follows. The oligonucleotides depicted in FIG. 5A are synthesized by conventional means using a commercial automated DNA synthesizer following the supplier's instructions. Odd numbered oligonucleotides in FIG. 5 are "sense" strands, even numbered oligonucleotides are "antisense" strands. Oligonucleotides 1 and 2, 3 and 4, 5 and 6, 7 and 8, 9 and 10, 11 and 12, 13 and 14 and 15 and 16 are annealed to each other, respectively, under conventional conditions, e.g. 10 mM tris, PH 7.5, 20 mM NaCl, 2 mM $MgCl_2$, and 10 pM (combined oligonucleotides)/$\lambda$ of solution, with heating to 100° C. followed by slow cooling over ~2 h to 37° C. The eight mixtures are then combined and the duplexes were ligated to one another under standard conditions, e.g. 50 mM tris, pH 7.4, 10 mM $MgCl_2$, 10 mM DTT, and 1 mM ATP and 5 Weiss units of T4 ligase (New England BioLabs) at room temperature overnight (~16 h). The mixture is electrophoresed through a 1% low gelling temperature agarose gel and a band of 480 bp was excised from the gel. That DNA molecule so produced encodes an Ala-125 IL-2 having the K→R mutations indicated above on an EcoRI/XhoI cassette.

b. Insertion into Vector, Expression and Modification of the LDV

The EcoRI/Xho I cassette may then be inserted into any desired vector, e.g. pxMT2 or derivatives thereof, using synthetic linkers as desired or necessary. Transformation of mammalian cells, e.g. COS or CHO cells, selection of transformants, amplification of gene copy number in the case of CHO transformants, and culturing of the cells so obtained to produce the desired LDV, may be readily effected by conventional methods, such as those disclosed in the references in Table 1, above.

The protein so produced may be recovered and further purified if desired, and PEGylated, and the PEGylated protein purified all by conventional methods.

Example 8: Preparation of Alternative PEGylated IL-2 LDV

Example 8 may be repeated using the oligonucleotides depicted in FIG. 5B in place of those depicted in FIG. 5A. The DNA molecule so produced encodes an LDV identical to that in Example 8, except that cystein at position 125 is retained. The corresponding PEGylated IL-2 LDV is thus produced.

Example 9: Preparation of PEG-ylated R-16, R-34, K-147 G-CSF LDV pxMT2G-CSF may be mutagenized by conventional procedures using oligonucleotides 16, 18 and 22 depicted in Example 5 to produce a pxMT2G-CSF derivative encoding the title G-CSF LDV. Transformation of mammalian cells, e.g. COS or CHO cells, selection of transformants, amplification of gene copy number in the case of CHO transformants, and culturing of the cells so obtained to produce the desired LDV, may be readily effected by conventional methods, such as those disclosed in the references in Table 1, above. The protein so produced may be recovered and further purified if desired, PEGylated by conventional procedures and the PEGylated protein purified by standard methods.

The same or similar procedures may be used by one skilled in the art to attach polymers such as PEG or PPG or other moieties, preferably hydrophilic moieties, to the other LDVs of the invention. Homogeneiety can be observed by conventional analysis of the modified LDVs so produced e.g. using standard SDS-PAGE or HPLC analysis.

Numerous modifications may be made by one skilled in the art to the methods and compositions of the present invention in view of the disclosure herein. Such modifications are believed to be encompassed by this invention as defined by the appended claims.

What is claimed is:

1. A polypeptide selected from the group consisting of G-CSF and erythropoietin having one or more lysine residues deleted, or replaced with an amino acid other than lysne, and containing at least one polyalkylene glycol moiety covalently attached to at least one amino acid residue of the polypeptide.

2. A method for preparing a polypeptide of claim 1 which comprises producing a modified form of the polypeptide in which one or more lysine residues are deleted or replaced with an amino acid other than lysine, reacting the modified polypeptide so produced with a polyalkylene glycol moiety under conditions permitting the covalent attachment of the moiety to the modified polypeptide, and recovering the product so produced from the reaction mixture.

3. A pharmaceutical composition containing a therapeutically effective amount of a polypeptide of claim 1 and a pharmaceutically acceptable carrier.

* * * * *